United States Patent
Darling et al.

(10) Patent No.: US 9,422,353 B2
(45) Date of Patent: *Aug. 23, 2016

(54) FIBROBLAST GROWTH FACTOR 21 VARIANT, COMPOSITION, AND USES THEREOF

(71) Applicant: Eli Lilly and Company, Indianapolis, IN (US)

(72) Inventors: Ryan James Darling, Fishers, IN (US); Craig Duane Dickinson, San Diego, CA (US); David Albert Driver, Solana Beach, CA (US); Malgorzata Donata Gonciarz, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/400,809

(22) PCT Filed: Jun. 5, 2013

(86) PCT No.: PCT/US2013/044192
§ 371 (c)(1),
(2) Date: Nov. 13, 2014

(87) PCT Pub. No.: WO2013/188182
PCT Pub. Date: Dec. 19, 2013

(65) Prior Publication Data
US 2015/0141327 A1 May 21, 2015

Related U.S. Application Data

(60) Provisional application No. 61/658,110, filed on Jun. 11, 2012.

(51) Int. Cl.
*A61K 38/18* (2006.01)
*C07K 14/50* (2006.01)
*A61K 38/00* (2006.01)

(52) U.S. Cl.
CPC .......... *C07K 14/50* (2013.01); *A61K 38/1825* (2013.01); *A61K 38/00* (2013.01)

(58) Field of Classification Search
None
See application file for complete search history.

(56) References Cited

U.S. PATENT DOCUMENTS 8,541,369 B2 * 9/2013 Dickinson .............. C07K 14/50 514/9.1
8,741,841 B2 * 6/2014 Darling .................. C07K 14/50 435/325
8,883,726 B2 * 11/2014 Dickinson .............. C07K 14/50 514/9.1
8,927,492 B2 * 1/2015 Darling .................. C07K 14/50 514/9.1
2012/0177646 A1 7/2012 Belouski et al.
2013/0085098 A1 4/2013 Dickinson et al.

FOREIGN PATENT DOCUMENTS

| EP | 1218509 | 4/2009 |
|---|---|---|
| EP | 2189475 | 5/2010 |
| WO | 03011213 | 2/2003 |
| WO | 2005061712 | 7/2005 |
| WO | 2005113606 | 12/2005 |
| WO | 2006028595 A2 | 3/2006 |
| WO | 2008121563 | 10/2008 |
| WO | 2009149171 | 12/2009 |
| WO | 2010042747 | 4/2010 |
| WO | 2010065439 | 6/2010 |
| WO | 2010084169 | 7/2010 |
| WO | 2010129503 | 11/2010 |
| WO | 2010129600 | 11/2010 |
| WO | 2011015349 | 12/2011 |

OTHER PUBLICATIONS

Patent Cooperation Treaty International Search Report and Written Opinion of the International Searching Authority pertaining to International Application No. PCT/US2013/044192. Date of Mailing: Sep. 3, 2013.
Berglund, Eric D., et al., Fibroblast Growth Factor 21 Controls Glycemia Via Regulation of Hepatic Glucose Flux and Insulin Sensitivity, Endocrinology, Sep. 2009, 150 (9), pp. 4084-4093.
Kharitonenkov, Alexei, et al., FGF-21 as a Novel Metabolic Regulator, J. Clin. Invest., 2005, 115 (6), pp. 1627-1635.
Kharitonenkov, Alexei, et al., The Metabolic State of Diabetic Monkeys is Regulated by Fibroblast Growth Factor-21, Endocrinology, 2007, 148 (2), pp. 774-781.
Kharitonenkov, Alexei, et al., Fibroblast Growth Factor-21 as a Therapeutic Agent for Metabolic Diseases, Biodrugs, 2008, 22 (1), pp. 37-44.
Micanovic, Radmila, et al., Different Roles of N- and C-Termini in the Functional Activity of FGF21, J. Cell. Physiol. 2009, 219: pp. 227-234.
Wente, Wolf, et al., Fibroblast Growth Factor-21 Improves Pancreatic β-Cell Function and Survival by Activation of Extracellular Signal-Reglated Kinase ½ and Akt Signaling Pathways, Diabetes, 2006, 55, pp. 2470-2478.
Wu, Xinle, et al., C-Terminal Tail of FGF19 Determines Its Specificity Toward Klotho Co-Receptors, J. Biol. Chem., Nov. 28, 2008, vol. 283, No. 48, pp. 33304-33309.
Yie, Junming, et al., FGF21 N- and C-Termini Play Different Roles in Receptor Interaction and Activation, FEBS Letters, 2009, 583 pp. 19-24.

* cited by examiner

*Primary Examiner* — Christine J Saoud

(57) ABSTRACT

This present invention relates to pharmacologically potent and stable human fibroblast growth factor 21 (FGF21) variants, pharmaceutical compositions comprising FGF21 variants, and methods for treating type 2 diabetes, obesity, dyslipidemia, and/or metabolic syndrome using such variants.

3 Claims, No Drawings

FIBROBLAST GROWTH FACTOR 21 VARIANT, COMPOSITION, AND USES THEREOF

This present invention relates to fibroblast growth factor 21 (FGF21) variants, pharmaceutical compositions comprising FGF21 variants, and methods for treating type 2 diabetes, obesity, dyslipidemia, and/or metabolic syndrome.

FGF21 is a hormone that functions as an important metabolic regulator of glucose and lipid homeostasis. FGF21 promotes glucose uptake in adipocytes by up-regulating GLUT1 expression, a mechanism distinct from that of insulin. In diabetic rodents and monkeys, human FGF21 lowered fasting serum concentrations of glucose, and reduced fasting serum concentrations of triglycerides, insulin and glucagon. Furthermore, in rodent models of diet induced obesity, FGF21 administration led to cumulative body weight loss in a dose dependent manner. Thus, FGF21 has potential utility for the treatment of diabetes, obesity, dyslipidemia, and metabolic syndrome.

Variants of human FGF21 have been described in WO2010/084169, WO2010/065439, WO2006/028595, and WO2005/061712.

Problems associated with human wild type FGF21 and known FGF21 variants are a low potency and/or pharmaceutical stability of the molecules. Thus, there is still a need for alternative FGF21 variants that are potent and/or stable.

The present invention provides alternative FGF21 variants. The FGF21 variants of the present invention have advantages over human wild type FGF21 and known FGF21 variants disclosed in the art. These advantages include having improved potency and/or improved pharmaceutical stability. In addition to improved potency, the FGF21 variants of the present invention have one or more advantageous stability characteristics that are useful for efficient manufacturing and/or formulation as a therapeutic protein, including reduced proteolytic degradation in vivo, reduced susceptibility to oxidation, lowered propensity to aggregate at high concentrations, lowered levels of post-translational modifications and proteolysis during production in mammalian cell systems, and/or improved chemical stability. Additionally, the FGF21 variants of the present invention are potentially useful for the treatment of type 2 diabetes, obesity, dyslipidemia, and/or metabolic syndrome.

The present invention provides a FGF21 variant, wherein the amino acid sequence is

```
                                              (SEQ ID NO: 1)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSFREDLK

EDGYNVYQSEAHGLPLHLPGDKSPHRKPAPRGPARFLPLPGLPPALPEPP

GILAPQPPDVGSSDPLRLVEPSQLRSPSFE.
```

The present invention also provides a pharmaceutical composition comprising a FGF21 variant of the present invention and at least one pharmaceutically acceptable carrier, diluent, or excipient.

The present invention also provides a method of treating type 2 diabetes, obesity, dyslipidemia, and/or metabolic syndrome in a patient comprising administering to the patient a FGF21 variant of the present invention.

The present invention also provides a method of treating type 2 diabetes, obesity, dyslipidemia, and/or metabolic syndrome in a patient comprising administering to the patient a pharmaceutical composition of the present invention.

Furthermore, the present invention provides a FGF21 variant of the present invention for use in therapy. Preferably, the present invention provides a FGF21 variant of the present invention for use in the treatment of type 2 diabetes, obesity, dyslipidemia, and/or metabolic syndrome.

Furthermore, the present invention provides the use of a FGF21 variant of the present invention in the manufacture of a medicament for the treatment of type 2 diabetes, obesity, dyslipidemia, and/or metabolic syndrome.

Full length human wild type FGF21 is a 208 amino acid polypeptide containing a 27 amino acid signal peptide. Mature human wild type FGF21 comprises the full length polypeptide without the 27 amino acid signal peptide, resulting in a 181 amino acid polypeptide (SEQ ID NO: 2). The changes in amino acid positions of the FGF21 variants of the present invention are determined from the amino acid positions in the polypeptide of mature human wild type FGF21 (SEQ ID NO: 2). Thus, a substitution described herein as "A31C" refers to substitution of the amino acid Cys for the wild type amino acid Ala at position 31 of the mature human wild type FGF21 variant.

It is important to note that a substitution of one amino acid residue in a particular variant may affect the characteristics of the variants as a whole, and that overall effect may be beneficial or detrimental to the pharmacological potency and/or pharmaceutical stability. For example, one amino acid substitution, P115W, increases the potency of the FGF21 variant, however P115W is also believed to contribute to the self-association that causes aggregation. Therefore, the overall effect is detrimental to the variants, and thus the substitution P115W is not included in the FGF21 variants of the present invention. Another example relates the amino acid substitution R175L, which increases the potency of the FGF21 variant. However, FGF21 variants having the R175L substitution were found susceptible to proteolysis, thus the overall effect was detrimental. To address the C-terminal proteolysis observed with the FGF21 variants of the present invention, amino acids at positions 180 and 181 (L at position 180 and G at position 181) are substituted with the amino acid E at position 180 and the amino acid at 181 is deleted. These modifications substantially decrease C-terminal proteolysis, but also reduce the pharmacological potency of the FGF21 variant by 25-fold measured in the human 293 cell-βKlotho-SRE luc assay. Surprisingly, potency is restored by reverting the amino acid residue at position 175 (R175L) back to the wild-type R. Therefore, the overall effect of this substitution is detrimental to the variants, and thus the substitution R175L is not included in the preferred FGF21 variants of the present invention.

FGF21 variants of the present invention are potent, biologically active variants as demonstrated for SEQ ID NO:1 in Example 2. The FGF21 variants of the present invention contain amino acid substitutions that together not only improve potency, but also are compatible with other amino acid changes that, in turn, provide for improved stability characteristics and increased in vivo stability. The amino acid substitutions in the FGF21 variants of the present invention that improve potency include D127K, S167R, and G174L (see Example 2).

Exposure of a concentrated variant solution of human wild type FGF21 to a pharmaceutical preservative, such as m-cresol, increases the propensity of the variant to form aggregates. Structural stabilization through the introduction of an additional disulfide bond improves the preservative compatibility as well as the thermal stability of human wild type FGF21. The FGF21 variants of the present invention incorporate the amino acid substitutions A31C and G43C that greatly improve thermal stability and preservative compatibility without compromising biological activity. High potency FGF21 variants that also include the A31C/G43C substitutions have been described previously. Those reported variants display significantly improved preservative compatibility relative to wild type FGF21, but they are still prone to aggregation in the presence of preservative. This variant aggregation increases the risk of immunogenicity, thereby reducing the acceptability of the variants as a therapeutic protein.

Surprisingly, the preferred FGF21 variants of the present invention include the amino acid substitutions L98D and L100K, which result in significantly lower high molecular weight aggregate formation at high concentrations. Advantageously, the amino acid substitutions L98D and L100K do not decrease the potency of the variants and minimize the detrimental aggregation problem.

A preferred commercial expression system for manufacture of the FGF21 variants of the present invention is the mammalian CHO-K1 cell line. However, the mammalian cell lines CHO-K1 and HEK293 may cause post-translational modifications to mature human wild type FGF21 through sulfation of the tyrosine side chain at position 179. Sulfation of tyrosine residues at positions 179 and 180 (if present) decreases potency and is an undesirable source of product heterogeneity. Thus, when an FGF21 variant having Tyr at position 179 and/or 180 is expressed from CHO-K1 or HEK293 cell lines, some proportion of the expressed variants may be sulfated at position 179, others may be sulfated at position 180, while others may be sulfated at both positions and some at neither position. This leads to a heterogeneous and unpredictable variant population with decreased potency.

The FGF21 variants of the present invention include an amino acid substitution that has resolved this detrimental sulfation. Thus, the amino acid substitution Y179F has been incorporated into the variants. Y179F eliminates the sulfation resulting from production in CHO-K1 and HEK293 cells. Moreover, the amino acid substitution Y179F is compatible with the other favored amino acid substitutions of the present invention, and is determined to be a neutral change with regard to potency.

Human wild type FGF21 is susceptible to proteolytic degradation in vivo. A major proteolytic fragment recovered from sera after intravenous or subcutaneous injection of mice or cynomolgus monkeys with wild type FGF21 is the fragment that terminates at position 171. The FGF21 fragment spanning residues 1 to 171 has been determined to be ~100-fold less potent in in vitro potency assays. Eliminating this proteolytic cleavage site may improve drug efficacy by increasing exposure to active drug. The amino acid substitution G170E has been shown to significantly slow cleavage in mouse and virtually eliminate proteolysis at the 171 position when measured after 24 hours in cynomolgus monkeys. The G170E substitution does not impact potency and is compatible with the desired physicochemical stability profile. Therefore, the amino acid substitution G170E is incorporated into the FGF21 variants of the present invention.

Human wild type FGF21 is also susceptible to a carboxypeptidase produced in CHO-K1 manufacture, and the amino acid substitution A180E and amino acid deletion at position 181 slows this processing, thereby reducing heterogeneity of the length of the variant expressed (i.e., heterogeneity in the number of amino acid residues in the mature variant expressed by the cell line). Although the amino acid substitution A180E and the amino acid deletion at position 181 do not eliminate C-terminal proteolysis in mammalian cell expression, it is quite effective at slowing proteolysis while maintaining the potency in the context of other desired amino acid substitutions found in the FGF21 variants of the present invention. In view of this advantageous characteristic, the amino acid substitution A180E and the amino acid deletion at position 181 are incorporated into the preferred FGF21 variants of the present invention.

The present invention also encompasses polynucleotides encoding the above-described variants that may be in the form of RNA or in the form of DNA, which DNA includes cDNA, and synthetic DNA. The DNA may be double-stranded or single-stranded. The coding sequences that encode the variants of the present invention may vary as a result of the redundancy or degeneracy of the genetic code.

The polynucleotides that encode for the variants of the present invention may include the following: only the coding sequence for the variants, the coding sequence for the variants and additional coding sequence, such as a leader or secretory sequence or a pro-variant sequence; the coding sequence for the variants and non-coding sequence, such as introns or non-coding sequence 5' and/or 3' of the coding sequence for the variants. Thus the term "polynucleotide encoding a variant" encompasses a polynucleotide that may include not only coding sequence for the variants but also a polynucleotide that includes additional coding and/or non-coding sequence.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The FGF21 variants of the present invention may readily be produced in mammalian cells such as CHO, NS0, HEK293 or COS cells; in bacterial cells such as *E. coli, Bacillus subtilis,* or *Pseudomonas fluorescence;* or in fungal or yeast cells. The host cells are cultured using techniques well known in the art. The preferred mammalian host cell is the CHOK1SV cell line containing a glutamine synthetase (GS) expression system (see U.S. Pat. No. 5,122,464).

The vectors containing the polynucleotide sequences of interest (e.g., the variants of FGF21 and expression control sequences) can be transferred into the host cell by well-known methods, which vary depending on the type of cellular host. For example, calcium chloride transformation is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, NY (1994).

The pharmaceutical compositions of the FGF21 variants of the present invention may be administered by any means known in the art that achieve the generally intended purpose to treat type 2 diabetes, obesity, dyslipidemia, and/or metabolic syndrome. The preferred route of administration is parenteral. The dosage administered will be dependent upon the age, health, and weight of the recipient, kind of concurrent treatment, if any, frequency of treatment, and the nature of the effect desired. Typical dosage levels can be optimized using standard clinical techniques and will be dependent on the mode of administration and the condition of the patient and can be determined by a person having ordinary skill in the art.

The FGF21 variants of the present invention are formulated according to known methods to prepare pharmaceutically useful compositions. A desired formulation is a stable lyophilized product that is reconstituted with an appropriate diluent or an aqueous solution of high purity with optional pharmaceutically acceptable carriers, preservatives, excipients or stabilizers [*Remington*, The Science and Practice of Pharmacy, 19th edition, Gennaro, ed., Mack Publishing Co., Easton, Pa. 1995].

The FGF21 variants of the present invention may be formulated with a pharmaceutically acceptable buffer, and the pH adjusted to provide acceptable stability, and a pH acceptable for administration. Moreover, the FGF21 compositions of the present invention may be placed into a container such as a vial, a cartridge, a pen delivery device, a syringe, intravenous administration tubing or an intravenous administration bag.

The term "dyslipidemia" means a disorder of lipoprotein metabolism, including lipoprotein overproduction or deficiency. Dyslipidemia may be manifested by elevation of the total cholesterol, low-density lipoprotein (LDL) cholesterol and the triglyceride concentrations, and/or a decrease in high-density lipoprotein (HDL) cholesterol concentration in the blood.

The term "metabolic syndrome" is characterized by a group of metabolic risk factors in one person. They include: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and/or, blood pressure of 130/85 or higher.

The term "obesity" is defined as a condition in which there is an excess of subcutaneous fat in proportion to lean body mass (Stedman's Medical Dictionary 28th edition, 2006, Lippincott Williams & Wilkins).

A "patient" is a mammal, preferably a human.

The term "treating" (or "treat" or "treatment") means slowing, reducing, or reversing the progression or severity of an existing symptom, disorder, condition, or disease.

The term "therapeutically effective amount" refers to the amount or dose of a variant of the present invention, as described herein, which, upon single or multiple dose administration to a patient, provides the desired treatment.

The term "type 2 diabetes" is characterized by excess glucose production in spite of the availability of insulin, and circulating glucose levels remain excessively high as a result of inadequate glucose clearance.

The present invention may be practiced by referencing the following examples. However, this is not to be interpreted as limiting the scope of the present invention.

EXAMPLE 1

Expression of FGF21 Variants in CHOK1SV Cells

The FGF21 variants of the present invention are produced in a mammalian cell expression system using CHOK1SV cells. Genes coding for FGF21 variants are subcloned into the Glutamine Synthetase (GS)-containing expression plasmid backbones (pEE12.4-based plasmids). The cDNA sequence encoding the FGF21 variants is fused in frame with the coding sequence of preferred signal peptide sequences to enhance secretion of the desired product into the tissue culture medium. The preferred signal peptide sequences are the polypeptides as shown in the amino acid sequences SEQ ID NO:3, SEQ ID NO:4, SEQ ID NO:5, or SEQ ID NO:6.

The expression is driven by the viral cytomegalovirus (CMV) promoter. CHOK1 SV cells are stably transfected using electroporation and the appropriate amount of recombinant expression plasmid, and the transfected cells are maintained in suspension culture, at the adequate cell density. Selection of the transfected cells is accomplished by growth in methionine sulfoximine (MSX)-containing serum-free medium and incubated at 35-37° C. and 5-7% $CO_2$.

Clonally-derived cell lines are measured and determined by use of a flow cytometer. The expression of an FGF21 variant in mammalian cells generally yields the natural N-terminal sequence, HPIP, i.e. without a methionine residue at the N-terminus, such as the FGF21 variant shown by the amino acid sequence of SEQ ID NO:1.

FGF21 variants secreted into the media from the CHO cells are purified by a process by which the clarified cell culture medium is heated to 50-60° C. for up to two hours, cooled, treated with detergent (Triton X-100) for viral inactivation, and is applied to a Capto MMC (GE Healthcare) mixed mode chromatography column. The FGF variant is eluted from the column using a pH 8 buffer, and the subsequent product pool is adjusted with 50 mM citric acid, 150 mM NaCl solution to a pH range of 3.2 to 3.5 for one hour for viral inactivation. The solution is adjusted to pH 6.7 to 7.3 by addition of Tris buffer and the FGF variant is further purified by hydrophobic exchange chromatography using Phenyl Sepharose High Performance resin (GE Healthcare). The hydrophobic interaction column is eluted with a decreasing gradient of sodium sulfate at pH 7. The HIC purified FGF variant is buffer exchanged into a Tris buffer at pH 8 containing NaCl and is further purified by anion exchange chromatography on Source 30Q resin (GE Healthcare). The anion exchange column is eluted with an increasing concentration of sodium chloride at pH 8. Purified FGF variant is passed through a Planova 20N (Asahi Kasei Medical) viral retention filter followed by concentration/diafiltration into 10 mM citrate, 150 mM NaCl pH 7 using tangential flow ultrafiltration on a regenerated cellulose membrane (Millipore).

EXAMPLE 2

3T3-L1-βKlotho Fibroblast Glucose Uptake Assay

3T3-L1-βKlotho fibroblasts are generated from 3T3-L1 fibroblasts by retroviral transduction of a CMV-driven mammalian expression vector containing the coding sequence of wild type mouse βKlotho and a blasticidin resistance marker. Blasticidin-resistant cells are selected after growth for 14 days in the presence of 15 μM blasticidin, and βKlotho variant expression is verified by immunoblot with an anti-βKlotho antibody. The 3T3-L1-βKlotho fibroblasts are maintained in Dulbecco's Modified Eagle Medium (DMEM) with 10% calf serum, and 15 μM blasticidin until plated for experimental use.

For glucose uptake, 3T3-L1-βKlotho fibroblasts are plated at 20,000 cells/well in 96-well plates and incubated for 48 hours in DMEM with 10% calf serum. The cells are incubated for 3 hours in DMEM with 0.1% bovine serum albumin (BSA) with or without an FGF21 variant of interest, followed by 1 hour incubation in Krebs-Ringer phosphate (KRP) buffer (15 mM Hepes, pH 7.4, 118 mM NaCl, 4.8 mM KCl, 1.2 mM $MgSO_4$, 1.3 mM $CaCl_2$, 1.2 mM $KH_2PO_4$, 0.1% BSA) containing 100 µM 2-deoxy-D-($^{14}$C) glucose with or without an FGF21 variant. Non-specific binding is determined by incubation of select wells in Krebs-Ringer bicarbonate/Hepes (KRBH) buffer containing 1 mM 2-deoxy-D-($^{14}$C) glucose. The reaction is terminated by addition of 20 µM cytochalasin B to the cells and glucose uptake is measured using a liquid scintillation counter.

The in vitro potency ($EC_{50}$) of the FGF21 variant of SEQ ID NO: 1 in the 3T3-L1-βKlotho fibroblast glucose uptake assay is 0.051 nM.

EXAMPLE 3

Physical Stability

Physical stability of FGF21 variants is determined as follows. Variants are dialyzed and prepared at 1-2 mg/mL in 10 mM Histidine pH7, with or without 150 mM NaCl and analyzed by SEC to determine the % HMW (Table 1: "Initial").

The SEC separation method is performed on a Tosoh Bioscience 3000SWXL, 5 micron column with dimensions 30 cm×0.78 cm. Mobile phase is 0.01 M citrate, 150 mM NaCl, pH 7 at a flow rate of 0.5 mL/minute. Initial low concentration samples are applied as 10 mcL injections and monitored at an absorbance wavelength of 214 nm, whereas the 30 mg/mL samples are applied as 1 mcL injections and monitored at 280 nm.

Next, variants are concentrated to 30 mg/mL and analyzed again (t=0). The % HMW for the FGF21 variant of SEQ ID NO: 7 increased from 0.15% to 0.9% upon concentration in histidine buffer in the presence of salt. The % HMW for the FGF21 variant of SEQ ID NO: 1 increased from 0.15% to 0.7% upon concentration in histidine buffer with salt. In the absence of salt the % HMW for the FGF21 variant of SEQ ID NO: 7 increased from 0.2% to 3.2% upon concentration and for FGF21 variant of SEQ ID NO: 1 increased from 0.13% to 1.0%. Thus, both the FGF21 variant of SEQ ID NO: 7 and the FGF21 variant of SEQ ID NO: 1 have lower initial % HMW and lower % HMW when variants are formulated at 30 mg/mL in the presence of 150 mM NaCl. These data demonstrate the importance of the L100K mutation that is present in the FGF21 variant of SEQ ID NO: 1, but not present in the FGF21 variant of SEQ ID NO: 7.

The 30 mg/mL formulations are incubated for 4 weeks at 4° C., 25° C., and 40° C. to assess longer-term stability under stress conditions. As shown in Table 1, the % HMW is determined again at 4 weeks time (t=4 weeks). The % HMW for the FGF21 variant of SEQ ID NO: 7 increased from 3.2% to 6.6% at 40° C. in the absence of salt. The % HMW for the FGF21 variant of SEQ ID NO: 1 increased from 1% to 5.3% at 40° C. The % HMW for the FGF21 variant of SEQ ID NO: 7 increased from 0.9% to 2.3% at 40° C. in the presence of salt and for FGF21 variant of SEQ ID NO: 1 increased from 0.7% to 1.7%. After 4 weeks at 25° C., levels of % HMW were only 1.1% for the FGF21 variant of SEQ ID NO: 1, whereas they were 2.9% for the FGF21 variant of SEQ ID NO: 7 in the absence of salt. These data demonstrate the beneficial impact of including the L100K mutation present in the FGF21 variant of SEQ ID NO: 1.

TABLE 1

Physical Stability

|  | Initial | 30 mg/mL % HMW (t = 0) | 30 mg/mL % HMW (t = 4 weeks) |
|---|---|---|---|
| FGF21 variant of SEQ ID NO: 7 | | | |
| 10 mM Histidine pH7, 150 mM NaCl | 0.15% | 0.9% | |
| 4° C. | | | 1.1% |
| 25° C. | | | 1.5% |
| 40° C. | | | 2.3% |
| 10 mM Histidine pH7 | 0.2% | 3.2% | |
| 4° C. | | | 2.5% |
| 25° C. | | | 2.9% |
| 40° C. | | | 6.6% |
| FGF21 variant of SEQ ID NO: 1 | | | |
| 10 mM Histidine pH7, 150 mM NaCl | 0.15% | 0.7% | |
| 4° C. | | | 0.8% |
| 25° C. | | | 0.8% |
| 40° C. | | | 1.7% |
| 10 mM Histidine pH7 | 0.13% | 1.0% | |
| 4° C. | | | 0.6% |
| 25° C. | | | 1.1% |
| 40° C. | | | 5.3% |

EXAMPLE 4

R175 and E180 Expression Heterogeneity

Production of a homogeneous variant product is desirable since it better ensures a consistent and well-characterized product. To assess product heterogeneity, a 10 µL aliquot of the sample is mixed with 90 µL of DPBS. The sample is analyzed by liquid chromatography-mass spectrometry (LC-MS), using the following conditions: the mobile phase A is 0.05% TFA, the mobile phase B is 0.04% TFA in acetonitrile, the column is a PLRPS 2.1×50 mm column, the injection volume is 15 µL.

TABLE 2

Gradient Conditions for Liquid Chromatographic Separation

| Time (min) | 0 | 1 | 15 | 16 | 20 | 20.1 | 30 |
|---|---|---|---|---|---|---|---|
| % B | 5 | 35 | 40 | 90 | 90 | 5 | 5 |
| Flow (µL/min) | 200 | 200 | 200 | 200 | 200 | 200 | 200 |

A Waters Micromass LCT Premier™ mass spectrometer is set up to a mass range between 400 to 1990 amu, polarity ES+, capillary 3000, sample cone 40 V, aperture 1 is 25 V, the source temperature is 105° C., cone gas flow is 50 L/hour, desolvation temperature is 150° C., and the desolvation gas flow is 600 L/hour.

TABLE 3

LC/MS Characterization of FGF21 Variants

| FGF21 Variant | 1-181 | 1-180 | 1-179 |
|---|---|---|---|
| FGF21 variant of SEQ ID NO: 7 | 33.7% | 63% | 3.3% |
| FGF21 variant of SEQ ID NO: 1 | 100% | | |

Table 3 reports the resulting heterogeneity in each FGF21 variant as determined by LC/MS method. The product 1-181 represents the full length FGF21 variant of SEQ ID NO: 7. The FGF21 variant of SEQ ID NO: 7 is susceptible to C-terminal truncations, especially removal of the amino acid residue glycine at position 181. As shown in Table 3, 33.7% of the purified product for the FGF21 variant of SEQ ID NO: 7 is the intended full-length 1-181; the 1-180 fragment makes up the largest portion of the purified product. In addition, minor amounts of product 1-179 are also detected.

The FGF21 variant of SEQ ID NO: 1 has the amino acid residue at 181 deleted in the genetic construct and amino acid residue 180 has been substituted to glutamic acid (E). These changes protect the C-terminus from degradation during CHO expression, resulting in 100% homogeneous purified 1-180 product.

EXAMPLE 5

Glucose Lowering in Ob/Ob Mouse Model

Male ob/ob mice and age-matched ob/m (lean) controls are 7 weeks of age upon arrival and 8-9 weeks of age at initiation of treatment. Upon arrival, all mice are single housed and allowed to acclimate for 1-2 weeks before the start of treatment. The mice are fed Purina Rodent Chow 5015 and given house water from an auto-water apparatus ad libitum. The mice are housed in 12-hour light/dark cycle with ambient temperature set at 75° F. One to two days prior to initiation of treatment, blood samples are collected via tail bleed. Blood glucose levels are measured using an Accu-Check Avivia blood glucose meter (Roche) and serum samples are collected for the assay of insulin using the Meso Scale mouse/rat insulin assay kit. On the day of treatment initiation (day 0), the mice are sorted into groups based on the pretreatment body weight, blood glucose, and serum insulin (BRAT sorting software). On day 0 and day 3, mice are dosed SQ with 0.1 to 30 nmol/kg of the FGF21 variant of SEQ ID NO: 5, in a volume of 10 ml/kg. Dosing vehicle is sterile PBS (HyClone DPBS/Modified-Calcium-Magnesium) containing 0.03% mouse serum albumin (MSA; Sigma A3139). Blood glucose is measured daily for 7 days and the AUC is determined $ED_{50}$ calculations for the glucose lowering are based on the AUC. Liver homogenates are collected at the time of sacrifice and liver triglycerides are measured on the Hitachi Modular P clinical analyzer.

On day 14, vehicle treated mice were hyperglycemic with mean blood glucose levels measured at 348±19.5 mg/dl (mean±SEM), while ob/m lean control mice had blood glucose levels of 165±3.2 mg/dl (mean±SEM). The FGF21 variant of SEQ ID NO: 1 lowered blood glucose to levels comparable to the ob/m lean controls. The $ED_{50}$ of the FGF21 variant of SEQ ID NO: 1 was 1.296 nmol/kg (95% confidence interval=–0.07-0.30).

Sequences

SEQ ID NO: 1 - FGF21 variant
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLK
EDGYNVYQSEAHGLPLHLPGDKSPHRKPAPRGPARFLPLPGLPPALPEPP
GILAPQPPDVGSSDPLRLVEPSQLRSPSFE SEQ ID NO: 2 - Wild Type FGF21 (Homo Sapiens)
HPIPDSSPLLQFGGQVRQRYLYTDDAQQTEAHLEIREDGTVGGAADQSPE
SLLQLKALKPGVIQILGVKTSRFLCQRPDGALYGSLHFDPEACSFRELLL
EDGYNVYQSEAHGLPLHLPGNKSPHRDPAPRGPARFLPLPGLPPALPEPP
GILAPQPPDVGSSDPLSMVGPSQGRSPSYAS SEQ ID NO: 3 - Human transferrin (hTrf) Signal Peptide
MRLAVGALLVCAVLGLCLA SEQ ID NO: 4 - Human fibroblast growth factor binding protein-1 (hFGFP-1) Signal Peptide
MKICSLTLLSFLLLAAQVLLVEG SEQ ID NO: 5 - Bovine lysozyme Signal Peptide
MKALVILGFLFLSVAVQG SEQ ID NO: 6 - Murine light chain (mkappa) Signal Peptide
METDTLLLWVLLLWVPGSTG SEQ ID NO: 7 - FGF21 variant
HPIPDSSPLLQFGGQVRQRYLYTDDAQQTECHLEIREDGTVGCAADQSPE
SLLQLKALKPGVIQILGVKTSRFLCQRPDGALYGSLHFDPEACSFREDLL
EDGYNVYQSEAHGLPLHLPGDKSPHRKPAPRGPARFLPLPGLPPALPEPP
GILAPQPPDVGSSDPLRLVEPSQLLSPSFLG SEQ ID NO: 8 - (DNA) FGF21 variant
CACCCCATCCCTGACTCCAGTCCTCTCCTGCAATTCGGGGGCCAAGTCCG
GCAGCGGTACCTGTACACCGACGACGCCCAGCAGACCGAGTGCCACCTGG
AAATCCGGGAGGACGGCACCGTGGGCTGTGCCGCCGACCAGTCCCCTGAG
TCCCTGCTGCAGCTGAAGGCCCTGAAGCCTGGCGTGATCCAGATCCTGGG
CGTGAAAACCTCCCGGTTCCTGTGCCAGAGGCCTGATGGCGCCCTGTACG
GCTCCCTGCACTTCGACCCTGAGGCCTGCTCCTTCCGGGAGGACCTGAAG
GAAGATGGCTACAACGTGTACCAGTCCGAGGCTCACGGCCTGCCTCTGCA
TCTGCCTGGCGACAAGTCCCCCCACCGGAAGCCTGCTCCTAGGGGCCCTG
CCAGATTCCTGCCACTGCCTGGCCTGCCTCCAGCTCTGCCTGAGCCTCCT
GGCATCCTGGCCCCTCAGCCTCCAGACGTGGGCTCCTCCGACCCTCTGCG
GCTGGTCGAGCCTTCCCAGCTGCGGAGCCCTAGCTTCGAG

We claim:

1. A fibroblast growth factor 21 (FGF21) variant, wherein the amino acid sequence of the variant is (SEQ ID NO: 1)
HPIPDSSPLLQFGGQVRQRYLYTDDAQQTECHLEIREDGTVGCAADQSPE

SLLQLKALKPGVIQILGVKTSRFLCQRPDGALYGSLHFDPEACSFREDLK

EDGYNVYQSEAHGLPLHLPGDKSPHRKPAPRGPARFLPLPGLPPALPEPP

GILAPQPPDVGSSDPLRLVEPSQLRSPSFE.

2. A pharmaceutical composition comprising the variant of claim 1, and at least one pharmaceutically acceptable carrier, diluent, or excipient.

3. A method of lowering blood glucose in a patient having type 2 diabetes, obesity, dyslipidemia, and/or metabolic syndrome, comprising administering the variant of claim 1 to a patient in need thereof.

* * * * *

SEQUENCE LISTING

<160> NUMBER OF SEQ ID NOS: 8

<210> SEQ ID NO 1
<211> LENGTH: 180
<212> TYPE: PRT
<213> ORGANISM: ARTIFICIAL
<220> FEATURE:
<223> OTHER INFORMATION: synthetic construct

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

```
Leu Glu Ile Arg Glu Asp Gly Thr Val Gly Cys Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Asp Leu Lys Glu Asp Gly Tyr Asn Val Tyr Gln Ser Glu Ala His
             100                 105                 110

Gly Leu Pro Leu His Leu Pro Gly Asp Lys Ser Pro His Arg Lys Pro
         115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Arg Leu Val Glu Pro Ser Gln Leu Arg Ser
                165                 170                 175

Pro Ser Phe Glu
            180

<210> SEQ ID NO 2
<211> LENGTH: 181
<212> TYPE: PRT
<213> ORGANISM: HOMO SAPIENS

<400> SEQUENCE: 2

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
             20                  25                  30

Leu Glu Ile Arg Glu Asp Gly Thr Val Gly Gly Ala Ala Asp Gln Ser
         35                  40                  45

Pro Glu Ser Leu Leu Gln Leu Lys Ala Leu Lys Pro Gly Val Ile Gln
 50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
             100                 105                 110

Gly Leu Pro Leu His Leu Pro Gly Asn Lys Ser Pro His Arg Asp Pro
         115                 120                 125

Ala Pro Arg Gly Pro Ala Arg Phe Leu Pro Leu Pro Gly Leu Pro Pro
130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 3
<211> LENGTH: 19
<212> TYPE: PRT
<213> ORGANISM: ARTIFICIAL
```

```
<220> FEATURE:
<223> OTHER INFORMATION: synthetic construct

<400> SEQUENCE: 3

Met Arg Leu Ala Val Gly Ala Leu Leu Val Cys Ala Val Leu Gly Leu
1               5                   10                  15

Cys Leu Ala

<210> SEQ ID NO 4
<211> LENGTH: 23
<212> TYPE: PRT
<213> ORGANISM: ARTIFICIAL
<220> FEATURE:
<223> OTHER INFORMATION: synthetic construct

<400> SEQUENCE: 4

Met Lys Ile Cys Ser Leu Thr Leu Leu Ser Phe Leu Leu Leu Ala Ala
1               5                   10                  15

Gln Val Leu Leu Val Glu Gly
            20

<210> SEQ ID NO 5
<211> LENGTH: 18
<212> TYPE: PRT
<213> ORGANISM: ARTIFICIAL
<220> FEATURE:
<223> OTHER INFORMATION: synthetic construct

<400> SEQUENCE: 5

Met Lys Ala Leu Val Ile Leu Gly Phe Leu Phe Leu Ser Val Ala Val
1               5                   10                  15

Gln Gly

<210> SEQ ID NO 6
<211> LENGTH: 20
<212> TYPE: PRT
<213> ORGANISM: ARTIFICIAL
<220> FEATURE:
<223> OTHER INFORMATION: synthetic construct

<400> SEQUENCE: 6

Met Glu Thr Asp Thr Leu Leu Leu Trp Val Leu Leu Leu Trp Val Pro
1               5                   10                  15

Gly Ser Thr Gly
            20

<210> SEQ ID NO 7
<211> LENGTH: 181
<212> TYPE: PRT
<213> ORGANISM: ARTIFICIAL
<220> FEATURE:
<223> OTHER INFORMATION: synthetic construct

<400> SEQUENCE: 7

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Cys His
            20                  25                  30

Leu Glu Ile Arg Glu Asp Gly Thr Val Gly Cys Ala Ala Asp Gln Ser
        35                  40                  45

Pro Glu Ser Leu Leu Gln Leu Lys Ala Leu Lys Pro Gly Val Ile Gln
    50                  55                  60
```

```
Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Asp Leu Leu Glu Asp Gly Tyr Asn Val Tyr Gln Ser Glu Ala His
            100                 105                 110

Gly Leu Pro Leu His Leu Pro Gly Asp Lys Ser Pro His Arg Lys Pro
            115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Arg Leu Val Glu Pro Ser Gln Leu Arg Ser
                165                 170                 175

Pro Ser Phe Leu Gly
            180

<210> SEQ ID NO 8
<211> LENGTH: 540
<212> TYPE: DNA
<213> ORGANISM: Artificial
<220> FEATURE:
<223> OTHER INFORMATION: synthetic construct

<400> SEQUENCE: 8
caccccatcc ctgactccag tcctctcctg caattcgggg gccaagtccg gcagcggtac      60
ctgtacaccg acgacgccca gcagaccgag tgccacctgg aaatccggga ggacggcacc    120
gtgggctgtg ccgccgacca gtcccctgag tccctgctgc agctgaaggc cctgaagcct    180
ggcgtgatcc agatcctggg cgtgaaaacc tcccggttcc tgtgccagag gcctgatggc    240
gccctgtacg gctccctgca cttcgaccct gaggcctgct ccttccggga ggacctgaag    300
gaagatggct acaacgtgta ccagtccgag gctcacggcc tgcctctgca tctgcctggc    360
gacaagtccc cccaccggaa gcctgctcct aggggccctg ccagattcct gccactgcct    420
ggcctgcctc cagctctgcc tgagcctcct ggcatcctgg cccctcagcc tccagacgtg    480
ggctcctccg accctctgcg gctggtcgag ccttcccagc tgcggagccc tagcttcgag    540
```